(12) United States Patent
Scott

(10) Patent No.: US 6,254,581 B1
(45) Date of Patent: Jul. 3, 2001

(54) PLEURAL CAVITY DRAINAGE DEVICE

(75) Inventor: Walter J. Scott, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 09/156,685

(22) Filed: Sep. 18, 1998

(51) Int. Cl.$^7$ .................................................. A61M 1/00

(52) U.S. Cl. ............................................................... 604/317

(58) Field of Search .................................... 604/317, 322, 604/323, 324, 349, 350; 600/573, 577, 578, 579

(56) References Cited

U.S. PATENT DOCUMENTS

| | | | |
|---|---|---|---|
| 5,207,661 | * | 5/1993 | Repsclager ............................ 604/317 |
| 5,211,642 | * | 5/1993 | Clendenning ......................... 604/410 |
| 5,616,138 | * | 4/1997 | Propp .................................... 604/317 |
| 5,772,625 | * | 6/1998 | Krueger et al. ....................... 604/317 |
| 5,865,793 | * | 2/1999 | Lo et al. ................................ 604/49 |

OTHER PUBLICATIONS

Heimlich, H.J., Diseases of the Chest 53(3):282–287 (1968).

Heimlich, H.J., JAMA 192(3):162 (1965).

McKennay, R. A., Ann Thores Surg 61:1115–1117 (1996).

Trachiots, G.D., et Ann Thorac Surg,65:1608–1613 (1996).

* cited by examiner

Primary Examiner—Kim M. Lewis
(74) Attorney, Agent, or Firm—Braman & Rogalskyj, LLP

(57) ABSTRACT

A device useful for draining fluid from the pleural cavity of a patient includes two enclosed chambers. The first chamber has at its upper end a one-way directional valve. The valve, which is provided with a connector for connection with a catheter draining fluid from the patient's pleural cavity, operates only to allow fluid to flow into the first chamber. The lower end of the first chamber, which is releasably connected to the second chamber, is optionally provided with a second one-way directional valve that operates only to allow fluid to flow from the first chamber into the second chamber. The second enclosed chamber of the device of the invention has an upper end and a closed lower end. The upper end of the second chamber is releasably connected to the lower end of the first chamber to provide a substantially fluid-tight connection. The device is provided with an outlet to the ambient atmosphere; the outlet can be disposed in either the first or the second enclosed chamber.

15 Claims, 2 Drawing Sheets

PLEURAL CAVITY DRAINAGE DEVICE

FIELD OF THE INVENTION

The present invention is directed to a medical device and, more particularly, to a device that provides for the drainage of fluid from the pleural cavity of a patient.

BACKGROUND OF THE INVENTION

Certain medical conditions such as pneumothorax (PTX), which is commonly observed in patients with acquired immunodeficiency syndrome (AIDS), can cause fluids to accumulate in the chest cavity, thereby repressing expansion of the lungs. Similarly, air, blood and other fluids can build up in the chest cavity postoperatively following heart or lung surgery. These conditions typically require insertion of a catheter into the patient's pleural cavity to allow fluid and air to drain away.

In 1968, Henry J. Heimlich in "Valve Drainage of the Pleural Cavity," *Dis. Chest,* 1968, Vol. 53, pages 282–286, described a device containing a flutter valve that could be connected to a catheter from a patient's chest cavity to allow the drainage of fluids while ensuring against the leakage of air into the cavity. Over the years, the "Heimlich valve" has found extensive use in the treatment of patients affected with PTX or recovering from thoracic surgery.

In use, the Heimlich valve is provided at its outlet end with a tube that extends into a plastic bag for the collection of fluids draining from the patient's chest cavity. The position of the bag needs to be adjusted to accommodate changes in the position of the patient. Because there is no seal between the bag and the outlet tube of the valve, there is considerable likelihood of fluid leakage or spillage of the bag's contents, especially if the patient desires to lie down. Furthermore, if an attempt is made to seal the bag, a dangerous build-up of pressure in the fluid collection could result.

Thus, although the Heimlich valve provides advantages over previously employed apparatus, there remains a need for a fluid collection device that can be used by a patient moving about or lying down without the risk of clothing or bedding being soiled by leaking fluid. This need is effectively met by the device of the present invention.

SUMMARY OF THE INVENTION

The present invention is directed to a device, useful for draining fluid from the pleural cavity of a patient, that includes two enclosed chambers. The first chamber has at its upper end a one-way directional valve. The valve, which is provided with a connector for connection with a catheter draining fluid from the patient's pleural cavity, operates only to allow fluid to flow into the first chamber. The lower end of the first chamber, which is releasably connected to the second chamber, is optionally provided with a second one-way directional valve that operates only to allow fluid to flow from the first chamber into the second chamber.

The second enclosed chamber of the device of the invention has an upper end and a closed lower end. The upper end of the second chamber is releasably connected to the lower end of the first chamber to provide a substantially fluid-tight connection. The device is provided with an outlet to the ambient atmosphere; the outlet can be disposed in either the first or the second chamber.

DETAILED DESCRIPTION OF THE INVENTION

Figure 1:
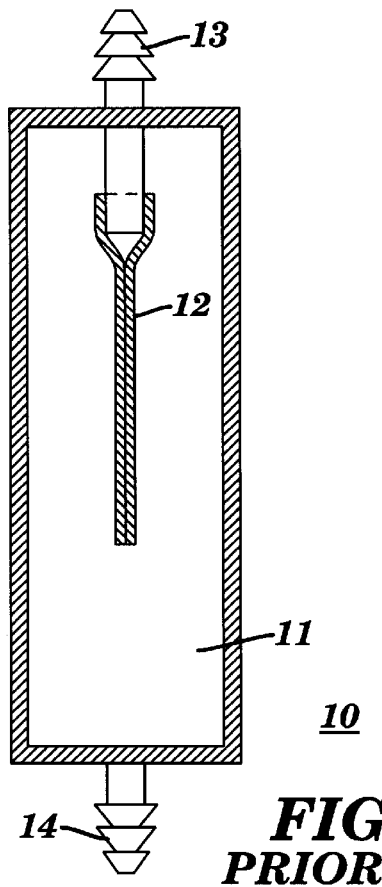
FIG. 1 is a schematic cross-section of a valve device of the prior art.

In FIG. 1 is schematically depicted a device 10 of the prior art, referred to as a "Heimlich valve". Device 10 includes an enclosed chamber 11 containing a flutter valve 12, which is provided with a connector 13 that can be attached to a patient's chest catheter (not shown). An outlet 14 can be connected to a tube (not shown), that allows fluid entering chamber 11 to exit for collection in a plastic bag (not shown).

Figure 2:
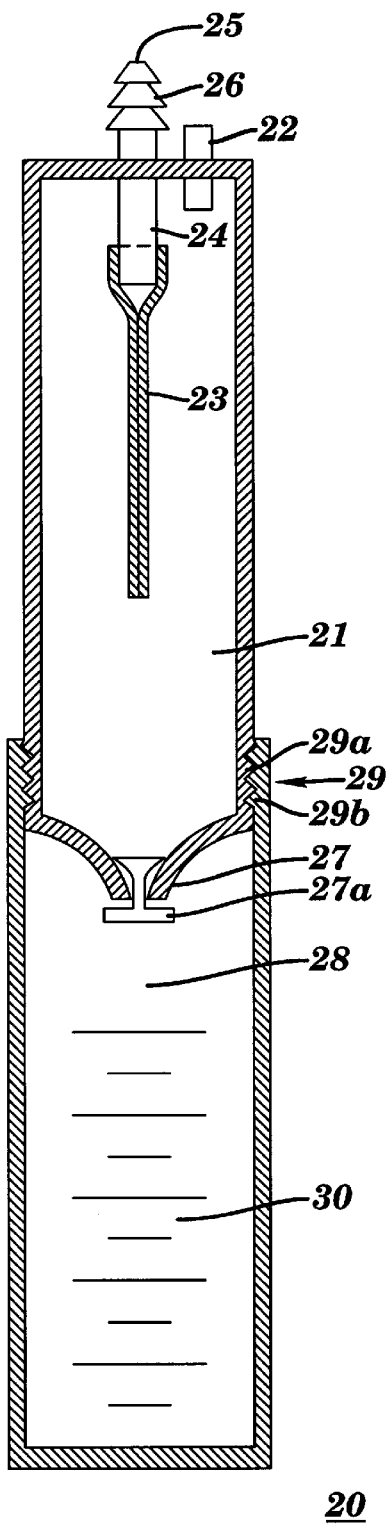
FIG. 2 is a schematic cross-section of an embodiment of the pleural cavity drainage device of the present invention.

FIG. 2 is a schematic representation in cross-section of device 20, an embodiment of the present invention. A first enclosed chamber 21 is provided with an outlet 22 to the ambient atmosphere, which prevents build up of pressure within device 20. Outlet 22 is depicted as a tube extending into first chamber 21. Also within chamber 21 is a first one-way directional valve 23, depicted as a flutter valve, that operates only to allow fluids and air to flow into first chamber 21 and prevents backflow into a patient's chest cavity. Valve 23 is provided with a connector 24, preferably having a tapered tip 25 with transverse corrugations 26, for attachment to a catheter (not shown) extending into a patient's chest cavity.

Device 20 further optionally includes at first chamber outlet 27 a second one-way directional valve 27a, preferably a check valve, which operates only to allow fluids and air to flow from first chamber 21 into a second chamber 28.

Outlet 27 of first chamber 21 may, if desired, be constructed to extend sufficiently far into second chamber 28 to prevent liquid in second chamber 28 from flowing back into first chamber 21 if the patient reclines. First chamber 21 and second chamber 28, which preferably are cylindrical in shape, are provided with connecting means 29 for releasably connecting chambers 21 and 28. Connecting means 29 are depicted in FIG. 2 as corresponding screw threads 29a and 29b on chambers 21 and 28, respectively, which provide a substantially fluid-tight connection. As fluid collects in second chamber 28, which is conveniently provided with volume indicator markings 30, the patient or a caregiver can readily disconnect chamber 28 from chamber 21 and pour out the accumulated fluid.

Figure 3:
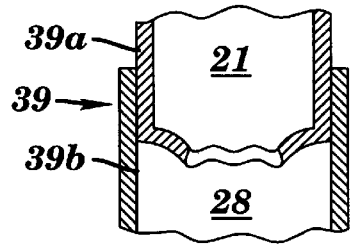
FIGS. 3 and 4 are schematic cross-sectional views of alternative connecting means for the chambers of the device of the present invention.
Figure 4:
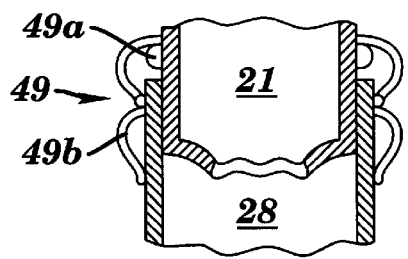

In FIGS. 3 and 4 are depicted alternative connecting means 39 and 49, respectively connecting chambers 21 and 28. Connecting means 39 comprises friction-adherable surfaces 39a and 39b on chambers 21 and 28, respectively. Connecting means 49 comprises clasp components 49a and 49b on chambers 21 and 28, respectively. Both connecting means 39 and 49, which permit ready separation of chambers 21 and 28, can be used with chambers of various shapes in addition to those having a cylindrical form. Chambers 21 and 28 are preferably constructed from a rigid plastic material, more preferably, one that is transparent or translucent.

Figure 5:
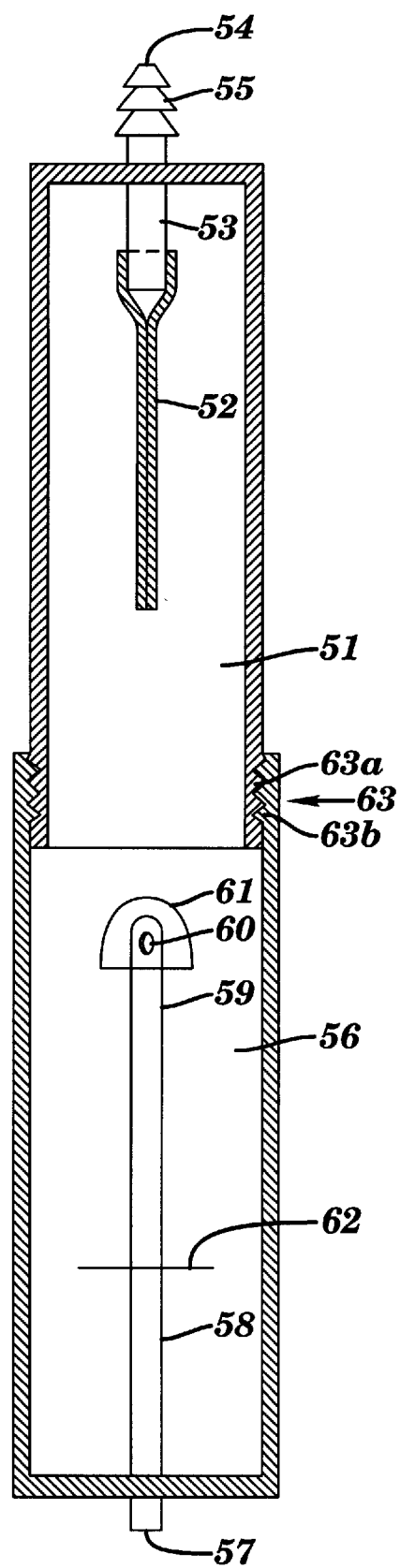
FIG. 5 is a schematic cross-section of another embodiment of the pleural cavity drainage device of the present invention.

FIG. 5 is a schematic representation in cross-section of device 50, another embodiment of the present invention. A first enclosed chamber 51 is provided with a one-way directional valve 52 that allows fluids and air to flow into first chamber 51 but prevents backflow into a patient's chest cavity. Valve 52 is provided with a connector 53 having a tapered tip 54 with transverse corrugations 55 that facilitates secure attachment of device 50 to a catheter (not shown) from a patient's chest cavity.

A second enclosed chamber 56 of device 50 is provided with an outlet 57 to the ambient atmosphere that includes a tube 58 extending into second chamber 57. At the distal end 59 of tube 58 is an orifice 60 and a shield 61 that prevents fluid dripping from valve 52 from entering orifice 60. Second chamber 56 can be further provided with a marking 62 that indicates when accumulated fluid should be emptied to ensure against its leakage through outlet 57.

Chambers 51 and 56 of device 50 further include releasable connecting means 63 represented as corresponding screw threads 63a and 63b, which provide a substantially fluid-tight connection.

The invention has been described in detail for the purpose of illustration, but it is understood that such detail is solely for that purpose, and variations can be made therein by those skilled in the art without departing from the spirit and scope of the invention, which is defined by the following claims.

What is claimed:

1. A device for providing drainage of fluid from the pleural cavity of a patient, said device comprising:

a first and a second enclosed chamber and an outlet to the ambient atmosphere from either said first or said second enclosed chamber;

said first enclosed chamber having an upper end and a lower end, said upper end comprising a first one-way directional valve provided with a connector for connecting said valve to a catheter for draining fluid from the pleural cavity of the patient, said first one-way directional valve operating only to allow fluid to flow into said first chamber, said lower end comprising means for releasably connecting said first chamber to said second chamber;

said second enclosed chamber having an upper end and a closed lower end, said upper end comprising means for releasably connecting said second chamber to said first chamber;

whereby said first chamber is connectable to said second chamber by said connecting means to provide a substantially fluid-tight connection.

2. The device of claim 1 wherein said outlet to the ambient atmosphere is included in said first enclosed chamber.

3. The device of claim 1 wherein said outlet to the ambient atmosphere is included in said second enclosed chamber.

4. The device of claim 1 wherein said lower end of said first chamber further comprises a second one-way directional valve operating only to allow fluid to flow from said first chamber into said second chamber.

5. The device of claim 1 wherein said connecting means of said first and second chambers are selected from the group consisting of screw threads, clasps, and friction-adherable surfaces.

6. The device of claim 1 wherein said first and second chambers each has a circular cross-section of substantially equal diameter.

7. The device of claim 6 wherein said connecting means of said first and second chambers comprise screw threads.

8. The device of claim 1 wherein said first one-way directional valve is a flutter valve.

9. The device of claim 4 wherein said second valve is a check valve.

10. The device of claim 1 wherein said first and second chambers each comprises a rigid plastic material.

11. The device of claim 10 wherein said rigid plastic material is transparent or translucent.

12. The device of claim 2 wherein said outlet to the ambient atmosphere comprises a tube extending into said first chamber.

13. The device of claim 3 wherein said outlet to the ambient atmosphere comprises a tube extending into said second chamber.

14. The device of claim 1 wherein said connector for connecting said first valve to a catheter comprises a tapered tip.

15. The device of claim 14 wherein said tapered tip has a transversely corrugated surface.

* * * * *